US010478578B2

(12) United States Patent
Esnouf

(10) Patent No.: US 10,478,578 B2
(45) Date of Patent: Nov. 19, 2019

(54) BOUGIE WITH A CONTROLLABLE TIP

(71) Applicant: Construct Medical Pty, Ltd., Woodend (AU)

(72) Inventor: Philip Stuart Esnouf, Richmond (AU)

(73) Assignee: Construct Medical Pty, Ltd., Woodend (AU)

( * ) Notice: Subject to any disclaimer, the term of this patent is extended or adjusted under 35 U.S.C. 154(b) by 563 days.

(21) Appl. No.: 15/034,890

(22) PCT Filed: Nov. 3, 2014

(86) PCT No.: PCT/AU2014/050329
§ 371 (c)(1),
(2) Date: May 6, 2016

(87) PCT Pub. No.: WO2015/066763
PCT Pub. Date: May 14, 2015

(65) Prior Publication Data
US 2016/0279365 A1      Sep. 29, 2016

(30) Foreign Application Priority Data

Nov. 6, 2013   (AU) .............................. 2013904281

(51) Int. Cl.
*A61M 16/04*        (2006.01)
*A61B 17/00*        (2006.01)

(52) U.S. Cl.
CPC .... *A61M 16/0488* (2013.01); *A61M 16/0418* (2014.02); *A61B 2017/003* (2013.01);
(Continued)

(58) Field of Classification Search
CPC .......... A61M 16/0488; A61M 16/0418; A61B 2017/003–00327; A61B 2017/00336; A61B 2017/0034
See application file for complete search history.

(56) References Cited

U.S. PATENT DOCUMENTS 3,802,440 A * 4/1974 Salem ............... A61M 16/0488
128/200.26
4,512,765 A    4/1985 Muto
(Continued)

FOREIGN PATENT DOCUMENTS

AU         2002-100213 A4    6/2002

OTHER PUBLICATIONS

International Search Report, dated Nov. 27, 2014.

*Primary Examiner* — Valerie L Woodward
(74) *Attorney, Agent, or Firm* — Banner & Witcoff, Ltd.

(57) ABSTRACT

A bougie for insertion in a patient, the bougie including:
(i) a main shaft having proximal and distal ends and a bore extending axially therein;
(ii) a movable tip having proximal and distal ends, the proximal end of the movable tip being connected to the distal end of the main shaft;
(iii) a control member having proximal and distal ends, the control member being mounted for sliding movement in the bore of the main shaft; and
(iv) the distal end of the control member being coupled to the distal end of the movable tip, the arrangement being such that an operator can slide the control member relative to the main shaft so as to cause displacement of the tip relative to the axial direction of the main shaft.

21 Claims, 11 Drawing Sheets

(52) U.S. Cl.
CPC ............... *A61B 2017/00309* (2013.01); *A61B 2017/00323* (2013.01); *A61M 2202/0208* (2013.01); *A61M 2205/583* (2013.01); *A61M 2205/587* (2013.01)

(56) References Cited

U.S. PATENT DOCUMENTS

| | | | | |
|---|---|---|---|---|
| 4,655,214 | A * | 4/1987 | Linder | A61M 16/0488 128/207.14 |
| 4,949,716 | A * | 8/1990 | Chenoweth | A61M 16/0418 128/207.14 |
| 5,127,393 | A | 7/1992 | McFarlin et al. | |
| 5,827,178 | A | 10/1998 | Berall | |
| 5,842,973 | A * | 12/1998 | Bullard | A61M 16/0488 600/194 |
| 6,415,787 | B1 * | 7/2002 | Boussignac | A61M 16/0488 128/200.26 |
| 6,668,832 | B2 | 12/2003 | Hipolito et al. | |
| 6,890,298 | B2 | 5/2005 | Berci et al. | |
| 8,505,531 | B2 * | 8/2013 | Pecherer | A61M 16/0488 128/200.26 |
| 9,010,320 | B2 * | 4/2015 | Furman | A61M 16/0418 128/200.26 |
| 9,199,051 | B2 | 12/2015 | Booth | |
| 9,265,908 | B2 | 2/2016 | Shockley | |
| 2008/0017195 | A1 | 1/2008 | Yoshida | |
| 2009/0192355 | A1 | 7/2009 | Mejia | |
| 2012/0073572 | A1 * | 3/2012 | Li | A61M 16/0488 128/200.26 |
| 2013/0199522 | A1 * | 8/2013 | Shockley | A61M 16/0488 128/200.26 |
| 2014/0123976 | A1 * | 5/2014 | Mccormick | A61M 16/0488 128/200.26 |
| 2015/0099935 | A1 * | 4/2015 | Runnels | A61M 16/0488 600/188 |

* cited by examiner

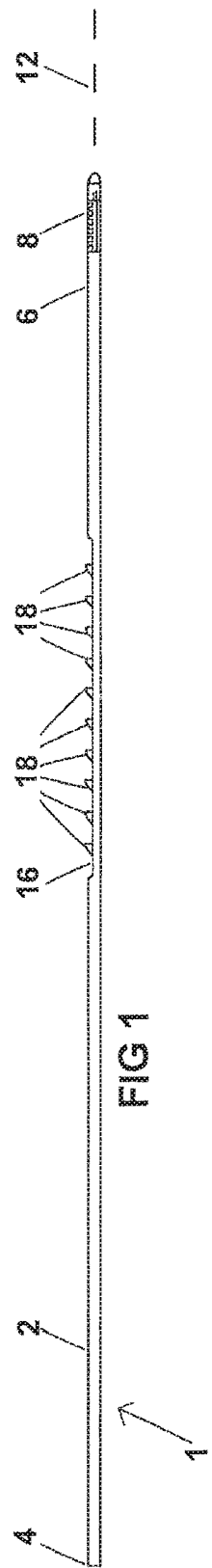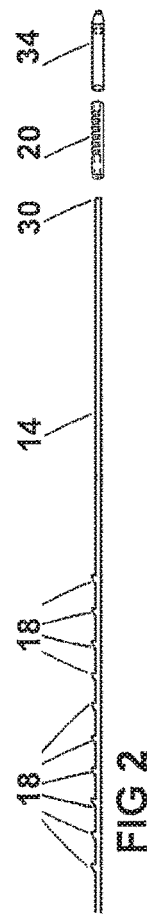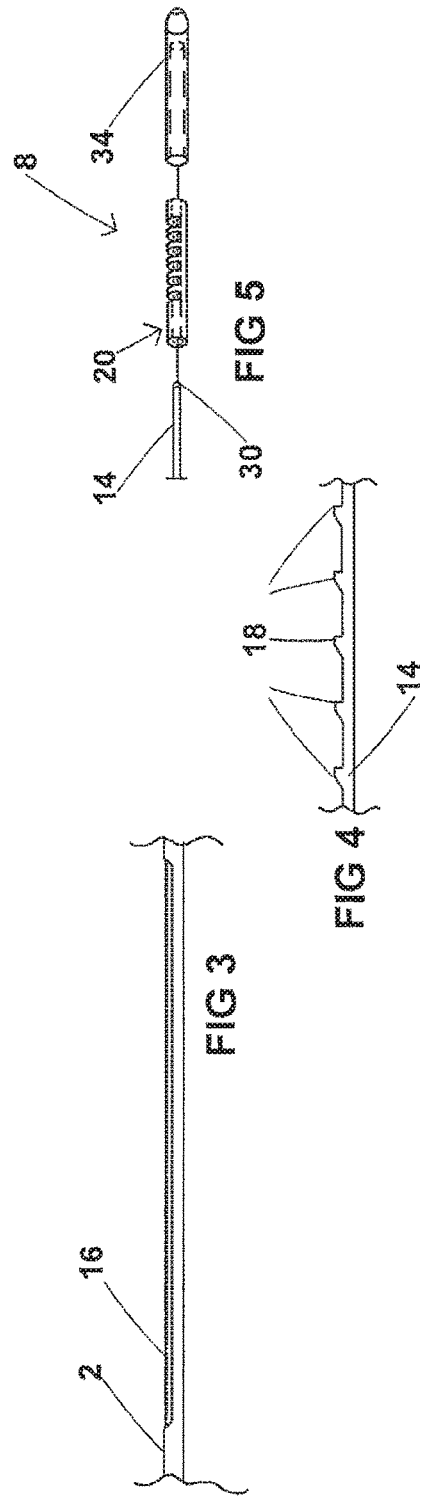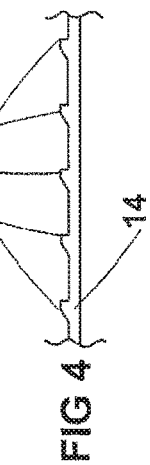
FIG 1
FIG 2
FIG 3
FIG 4
FIG 5

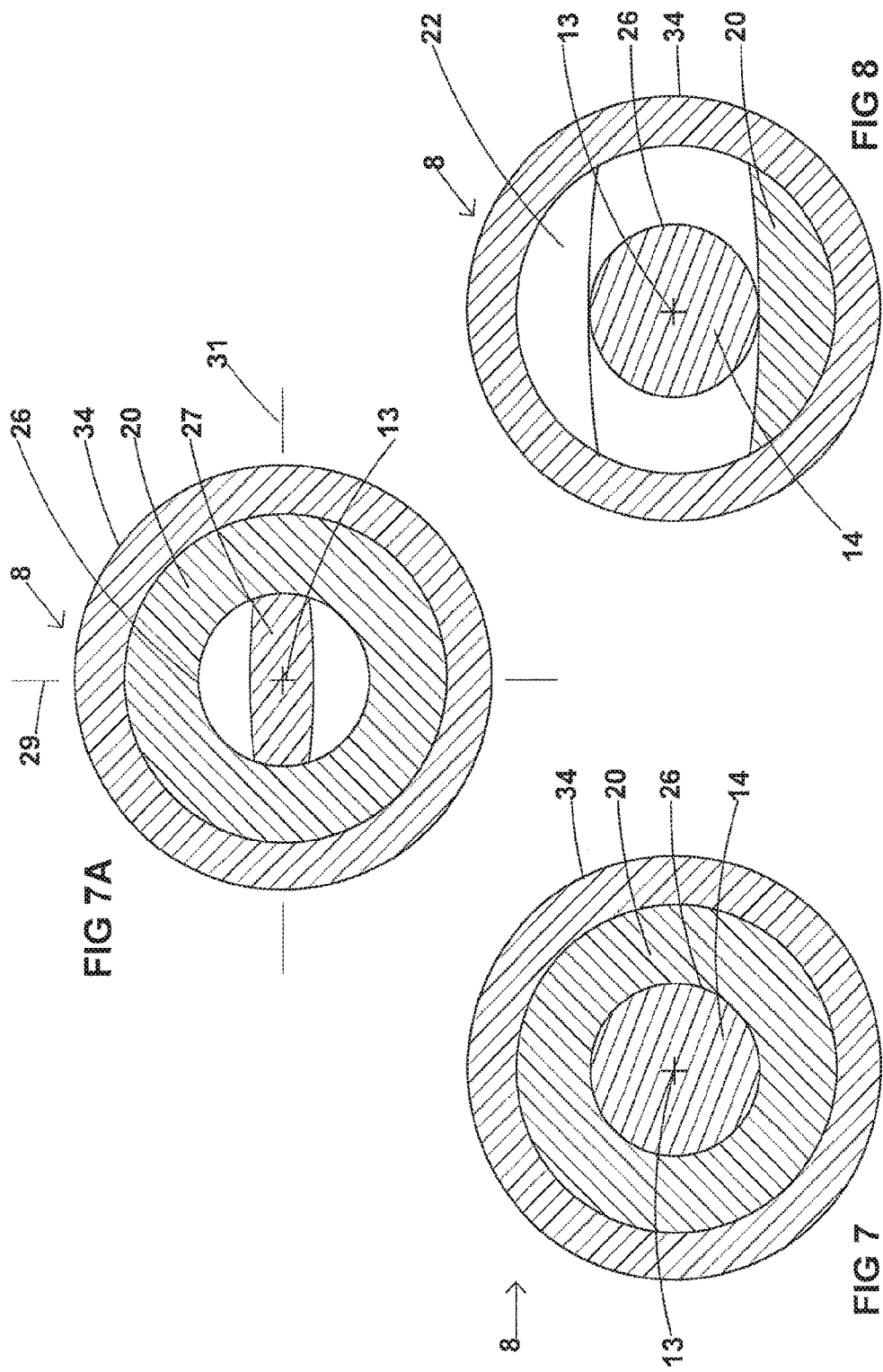

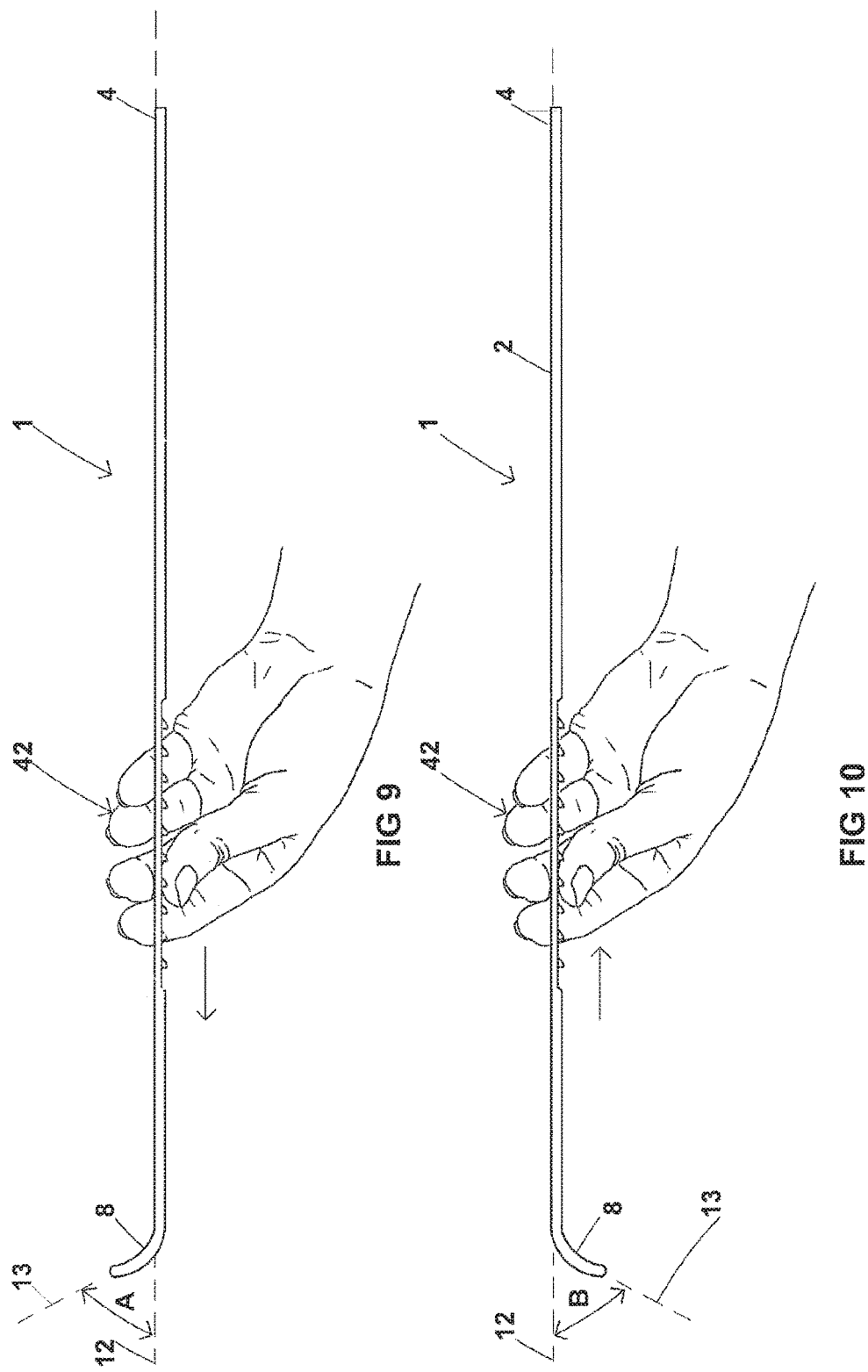

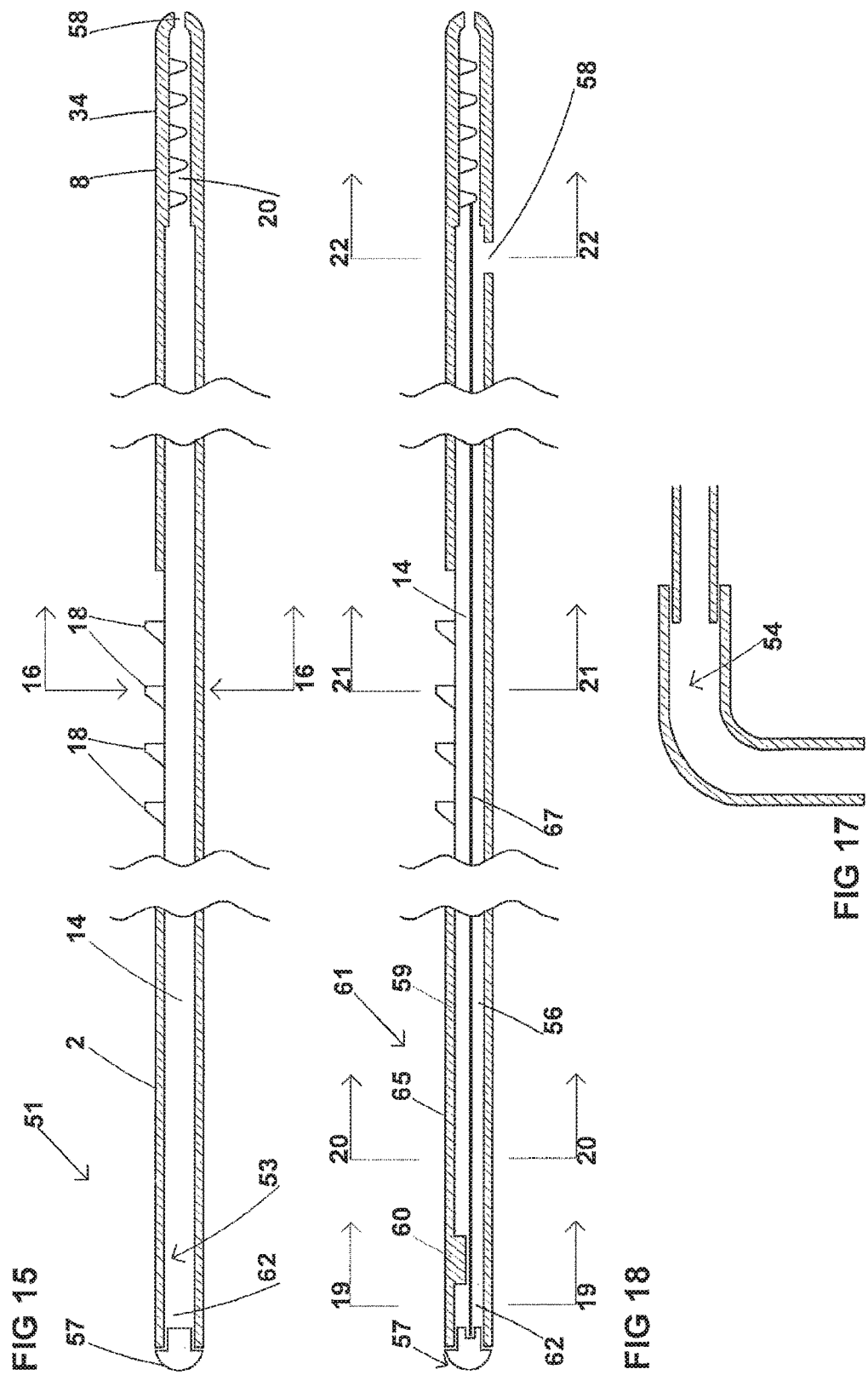

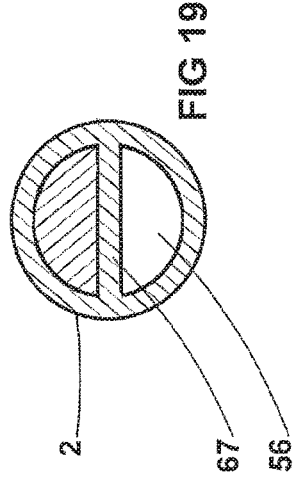
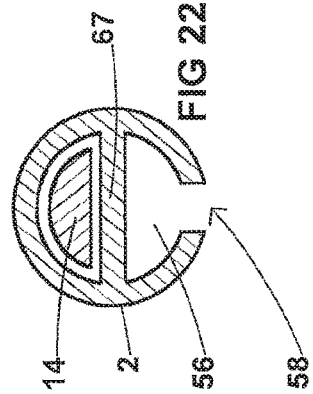
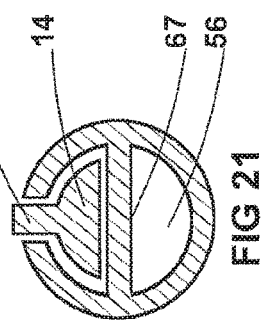
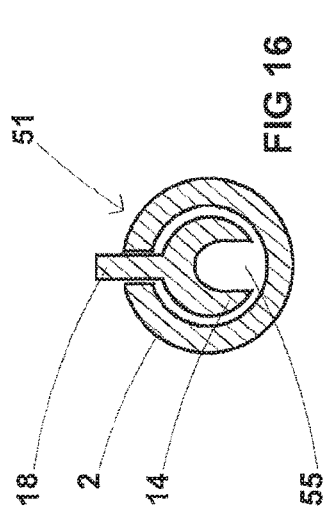
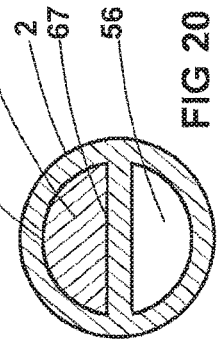

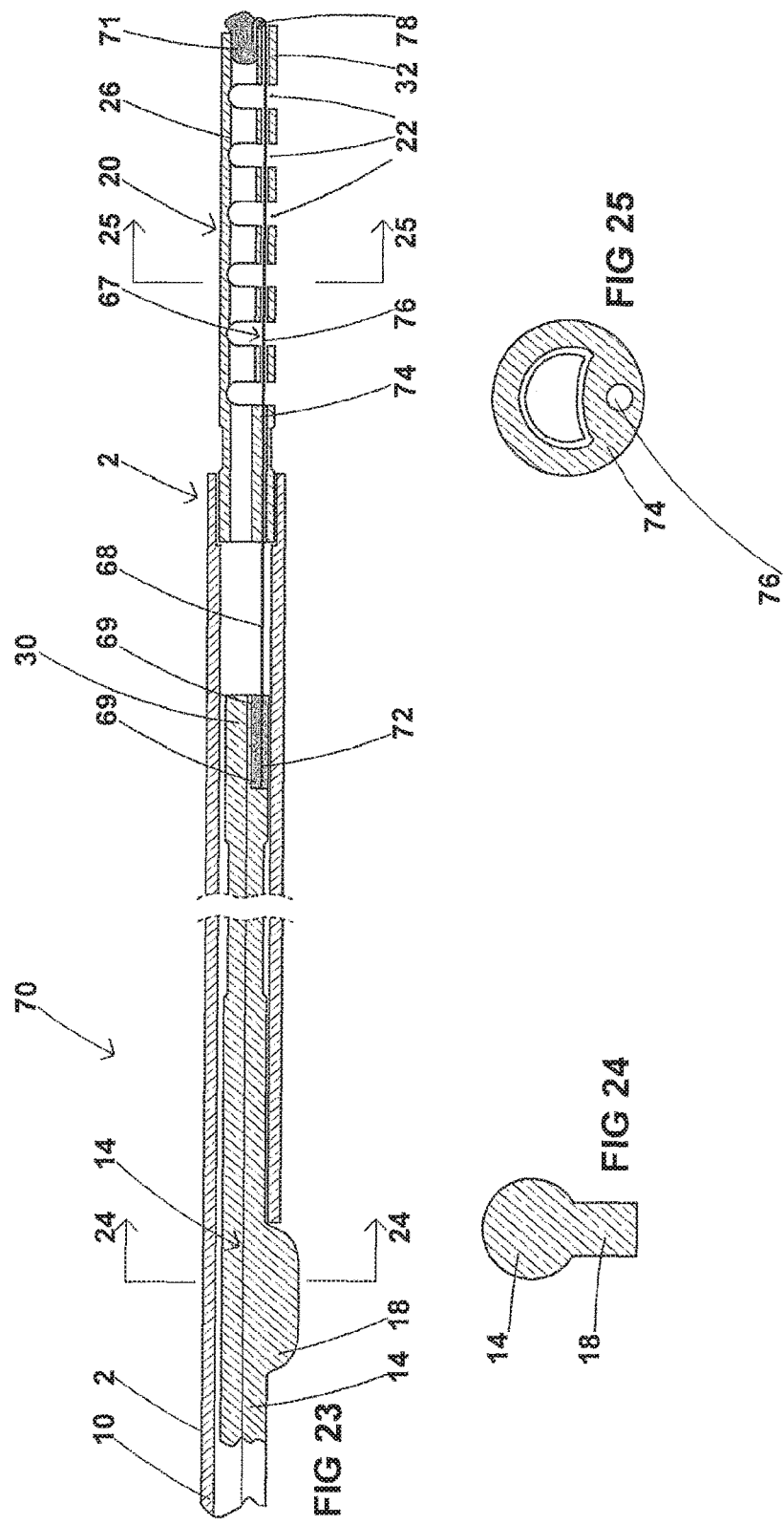

BOUGIE WITH A CONTROLLABLE TIP

The application is a U.S. National Phase Entry of International Application No. PCT/AU2014/050329 filed on Nov. 3, 2014, designating the United States of America and claiming priority to Australian Patent Application No. 2013904281 filed on Nov. 6, 2013. The present application claims priority to and the benefit of the above-identified applications and the above-identified applications are incorporated by reference herein in their entireties.

FIELD OF THE INVENTION

This invention relates to a bougie with a controllable tip.

BACKGROUND

The introduction of an endotracheal tube (ETT) into the trachea is a common medical procedure performed during resuscitation and anaesthesia. It is referred to as "intubation" and is intended to provide a secure airway in patients who are unable to manage their breathing. Greater than 4.5 million intubations occur worldwide per year.

This is usually performed under direct vision using a laryngoscope. Laryngoscopes come in a variety of patterns but essentially comprise a light source, a blade and a handle. Using the blade as a spatula the laryngoscope is inserted through the mouth behind the base of the tongue and is then placed above the larynx in order to visualise the vocal cords (chords). Once the laryngoscope is in place an endotracheal tube is guided manually under direct vision between the chords and into the upper trachea. Recently a number of video laryngoscopes have become available, these devices are designed to provide a clearer view of the vocal chords and surrounding structures by virtue of a camera being placed close to the tip of the blade. The image from this camera is typically displayed on a screen attached to the handle of the video-laryngoscope, or placed remotely, but within visual range of the operator.

There are a number of situations that can make intubation difficult and in some cases impossible. These include an inability to sufficiently open the mouth due to trauma, inability to flex or extend the neck due to trauma or pathology in the cervical spine or distortion of the anatomy surrounding the glottis due to tumours, haemorrhage, etc. The inability to intubate a patient can constitute a medical emergency and in some cases can result in death. A number of techniques have been developed to help clinicians overcome some of these difficult situations.

One technique is the use of a guide or a bougie to negotiate a pathway between the vocal chords. Once a bougie is successfully in place an endotracheal tube can be placed over the bougie and slid down to follow the bougie through the chords, this technique is commonly referred to as "railroading".

The advantage of placing the bougie through the chords is that it is of a significantly smaller diameter (typically 4-5 mm) in comparison to the ETT which can range from 5-12 mm. This allows much greater visibility when guiding the bougie through the chords. With both conventional and video laryngoscopes a large diameter ETT can obscure vision of the chords. The ETT is normally moulded with a curve that allows it to follow the curved pathway from the oral opening to the chords. However, in many cases the angle at which the tip of the ETT presents itself to the opening between the chords does not allow the ETT tube to negotiate this space. Furthermore, the bougie can be made from relatively stiff material which is easier to control in terms of guiding it through the chords. Additionally, the end of the bougie may be formed with an angled tip, which provides the capacity to manoeuvre the tip through the chords by rotating the bougie so the tip can be positioned optimally to advance.

A number of bougies are currently available for this purpose and are designed using different materials, diameters and tip angles.

There are, however, occasions where the tip angle is insufficient or too great to position these bougies within the chords.

Additionally, in some circumstance it is helpful to be able to introduce oxygen into the patient's airway during the intubation process. Therefore some bougies have an internal passageway to channel oxygen from the proximal end to the distal end of the bougie, that is they are hollow. When additional oxygen is used in this way, it may be introduced in a manner that assists in ventilation. This can occur by the entrainment of air into the trachea, a technique known as jet ventilation or the agitation of surrounding air this technique is known as high frequency jet ventilation.

SUMMARY OF THE INVENTION

According to the present invention there is provided a bougie for insertion in a patient, the bougie including:
  (i) a main shaft having proximal and distal ends and a bore extending axially therein;
  (ii) a movable tip having proximal and distal ends, the proximal end of the movable tip being connected to the distal end of the main shaft;
  (iii) a control member having proximal and distal ends, the control member being mounted for sliding movement in the bore of the main shaft; and
  (iv) the distal end of the control member being coupled to the distal end of the movable tip, the arrangement being such that an operator can slide the control member relative to the main shaft so as to cause displacement of the tip relative to the axial direction of the main shaft.

Preferably the tip includes a tip body with lateral formations which, when the body is subject to pulling or pushing by the control rod, causes lateral displacement of the tip in anterior and posterior directions respectively.

Preferably further the body is tubular and the lateral formations comprise slots extending laterally through the tubular body along one side of the tubular body.

Preferably further, the control rod extends through the tubular body and its distal end is coupled to the distal end of the tubular body so that:
  (i) when the operator slides the control rod in a proximal direction relative to the main shaft the tip is displaced in the anterior direction; and
  (ii) when the operator slides the control rod in a distal direction relative to the main shaft the tip is displaced in the posterior direction.

An additional feature is the addition of a channel running the entire length of the device to allow the passage of oxygen from the proximal end to the distal end. The proximal end may have a removable cover to allow coupling of an oxygen supply tube. The channel may terminate at the tip of the bougie via a concentric port or, alternatively, it may terminate via a side port in the distal end of the main shaft in close proximity to the displaceable tip.

The oxygen may pass through the existing hollow formation of the main shaft and displaceable tip with an additional channel formed in the lateral aspect of the control shaft opposite to the lateral projections. Alternatively, a specific channel may be formed within the main shaft for this purpose.

BRIEF DESCRIPTION OF THE DRAWINGS

FIG. 1 is a side view of a bougie constructed in accordance with the invention;

FIG. 2 is a schematic exploded view of the bougie of the invention;

FIG. 3 is a fragmentary view showing a slot in the main shaft of the bougie;

FIG. 4 is a fragmentary view of part of the control rod of the bougie;

FIG. 5 is a fragmentary exploded view of the tip of the bougie;

FIG. 7 is a cross-sectional view along the line 7-7;

FIG. 7A is a similar view to FIG. 7 through an alternative embodiment of the invention;

FIG. 8 is a cross-sectional view along the line 8-8;

FIG. 9 shows operation of the bougie in order to produce deflection in a posterior direction;

FIG. 10 is a schematic view showing operation of the bougie to produce deflection in an interior direction;

FIG. 15 is a schematic longitudinal view through a modified bougie of the invention having an oxygen port therein;

FIG. 16 is a cross-sectional view along the line 16-16;

FIG. 17 is a schematic view of the oxygen inlet port;

FIG. 18 is an alternative bougie of the invention with an oxygen port;

FIG. 19 is a cross-sectional view along the line 19-19;

FIG. 20 is a cross-sectional view along the line 20-20;

FIG. 21 is a cross-sectional view along the line 21-21;

FIG. 22 is a cross-sectional view along the line 22-22;

FIG. 23 is a fragmentary longitudinal cross-section through a further alternative embodiment of the invention;

FIG. 24 is a cross-sectional view along the line 24-24; and

FIG. 25 is a cross-sectional view along the line 25-25.

DETAILED DESCRIPTION

Figure 6:
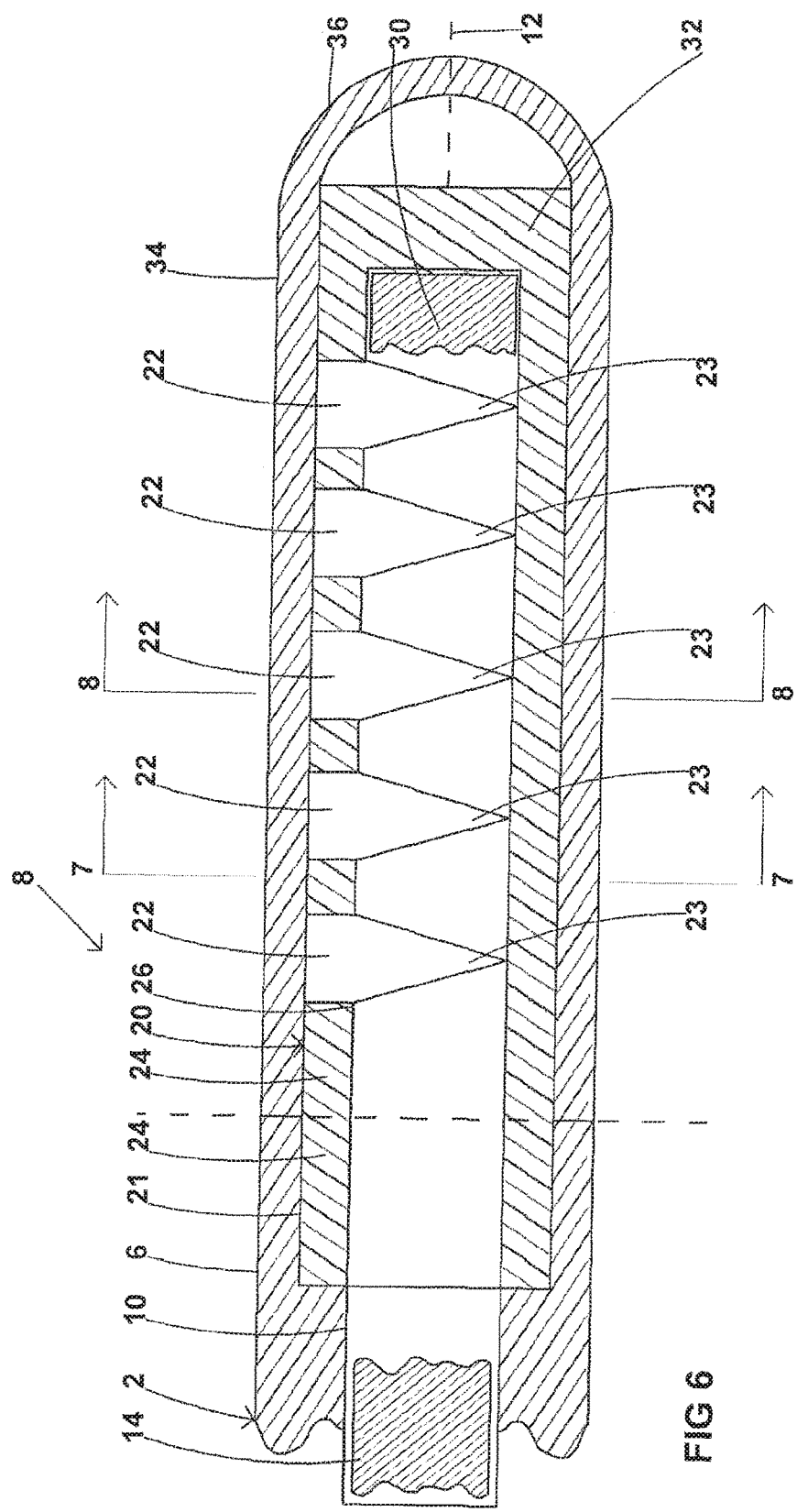
FIG. 6 is an enlarged axial cross-sectional view of the tip of the bougie.

FIG. 1 schematically shows a bougie 1 of the invention. It includes a main shaft 2 having a proximal end 4 and a distal end 6. A displaceable tip 8 is located at the distal end of the main shaft 2. The main shaft 2 is preferably in the form of a nylon tube having a length of about 600 mm. It is preferred that the outer diameter is about 4 mm and it has an internal bore 10 which is 3 mm in diameter, as seen in FIG. 6. The tip 8 can be displaced relative to the longitudinal axis 12 of the main shaft 2. As will be described in more detail below, the orientation of the tip 8 relative to the axis 12 can be controlled by means of a control rod 14 which is slidably mounted within the bore 10 of the main shaft 2.

In the preferred form of the invention, the proximal end 4 of the main tube is closed and a longitudinally extending recess 16 is formed in the shaft 2 in order to permit access by an operator to the control rod 14. As best seen in FIG. 2, the control rod 14 includes lateral projections 18 which are located in the region of the recess 16 so that they are manually accessible to an operator. As best seen in FIGS. 9 and 10, an operator can grasp the bougie 1 of the invention and use his or her fingers or thumb to grip the projections 18 on the control rod 14 so that it can be axially moved within the main shaft 2 and this movement can be used to control deflection of the tip 8 relative to the axis 12. FIG. 9 shows the axis 13 of the tip deflected through an angle A in a posterior direction. FIG. 10 shows the axis 13 of the tip deflected through an angle B in the anterior direction.

As seen in FIGS. 5 to 8, the tip includes a tip body 20 which is preferably formed of a relatively short length of nylon tube, the length of which is in the range from 25 to 35 mm and preferably about 30 mm. It is preferred that the outer diameter of the body 20 is intermediate of the outer diameter and bore diameter of the main shaft 2. In this way, the distal end 6 of the main shaft 2 can be formed with a rebate 21 which can receive the proximal end 24 of the body 20, as shown in FIG. 6. In FIG. 6, part of the control rod 14 is not shown for clarity of illustration. The body is formed with a plurality of transversely extending slots 22. The arrangement is such that when the distal end of the body 20 is subjected to tension, it will tend to distend towards the side in which the slots are formed and in the opposite direction when subjected to compression, as will be described in more detail below. After tension or compression the natural elasticity of the material of the body will return it to a relaxed position in which its axis 13 is aligned with the axis 12 of the main shaft 2.

In an alternative arrangement, the tip body 20 could be integrally formed at the distal end of the main shaft 2.

The proximal end 24 of the tip body 20 is glued or bonded to the rebate 21 of the main shaft 2 so that the bore 26 of the body 20 is aligned and generally contiguous with the bore 10 of the main shaft 2, as seen in FIG. 6 (i.e. the axes 12 and 13 are concentric).

The control rod 14 is preferably moulded from nylon rod having a diameter of 2.8 mm so that it is freely slidable within the bores 10 and 26. In the region where the projections 18 are located, the cross-sectional shape of the rod 14 is flattened so that the projections 18 are more prominent. Preferably the outer surface of the shaft 2 adjacent to the recess 16 is roughened or contains projections (not shown) to facilitate the user gripping the main shaft 2 and enabling better control of the movement of the control rod 14.

In FIG. 6 it will be seen that the distal end 30 of the control rod 14 is joined to a closed distal end 32 of the tip body 20. The tip 8 includes a flexible sheath 34 which is in the form of a sleeve of silicon rubber having a rounded closed distal end 36 and a proximal end 38 which is glued or bonded to the proximal end 24 of the body 20. It is preferred that the outer diameter of the sheath 34 is the same as or approximately the same as the outer diameter of the main shaft 2.

In the illustrated arrangement, the slots are located on one side only of the tip body 20. The provision of asymmetrically located slots 22 enable the tip body 20 to be rotated, laterally displaced or bent laterally because of expansion or contraction of the slots 22 when subjected to tensile or compressive forces from the control rod 14. In this arrangement the inner ends 23 of the slots 22 are V-shaped so that each slot has an apex which enhances bending of the tip body 20 when the control rod 14 is moved. A similar effect could also be obtained if the inner ends 23 of the slots 22 were curved or rounded. More particularly, if the control rod 14 moves in a proximal direction (to the left), as seen in FIG. 6, the body 20 will be displaced or rotated upwardly relative to the axis 12. Preferably this displacement in an anterior direction is about 100°. In the illustrated arrangement the control rod has a range of movement of about 3 to 5 mm and preferably about 4 mm either side of a neutral position (in which the tip 8 is aligned with the main shaft 2). On the other hand, if the control rod 14 is moved in the distal direction (to the right), the body 20 will be displaced or rotated in the posterior direction preferably by an amount of up to about 90° relative to the axis 12. Movement of the control rod is limited by the endmost projections 18 engaging the ends of recess 16. As indicated above, an operator can grip the projections 18 of the main shaft 2 and cause movement of the control rod 14 in either a proximal or distal direction in order to cause displacement in anterior or posterior directions, as diagrammatically illustrated in FIGS. 9 and 10. It is to be understood that the terms anterior and posterior are used for convenience and are the normal positions as shown in FIGS. 9 and 10. It is to be understood, of course, that the bougie of the invention can be used in any orientation.

In the preferred embodiment, the portion 27 of the control rod 14 which is located within the bore 26 of the body 20 is flattened so that it has good flexure in the anterior and posterior directions as diagrammatically illustrated in FIG. 7A. This facilitates in stiffening the body 20 against displacement in directions other than the posterior and anterior directions (i.e. perpendicularly relative to these directions). It will also be appreciated that the shape of the body 20 with the lateral slots 22 also facilitates in providing flexibility in the anterior and posterior directions whilst resisting deflections in directions perpendicular thereto. More particularly, the flattened shape of the portion 27 of the control rod and the orientation of the slots 22 is such that the deflection of the tip 8 occurs most easily in a plane 29 which includes the axis 12 and is transverse to the lateral direction of the slots 22. It also follows that the tip 8 is more resistant to deflection in a plane 31 which is orthogonal to the plane 29, as shown in FIG. 7A.

Figure 11:
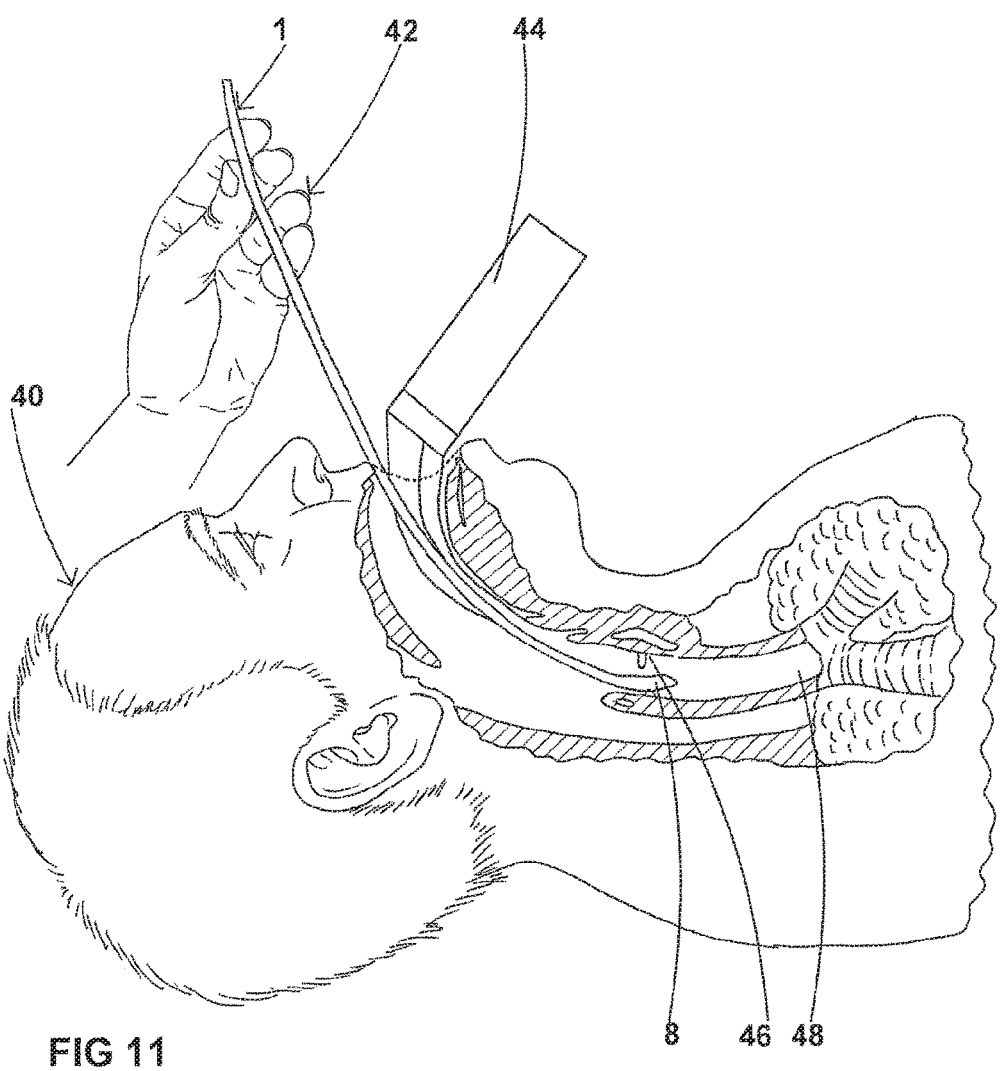
FIG. 11 is a schematic view showing insertion of the bougie through the chords of a patient.
Figure 12:
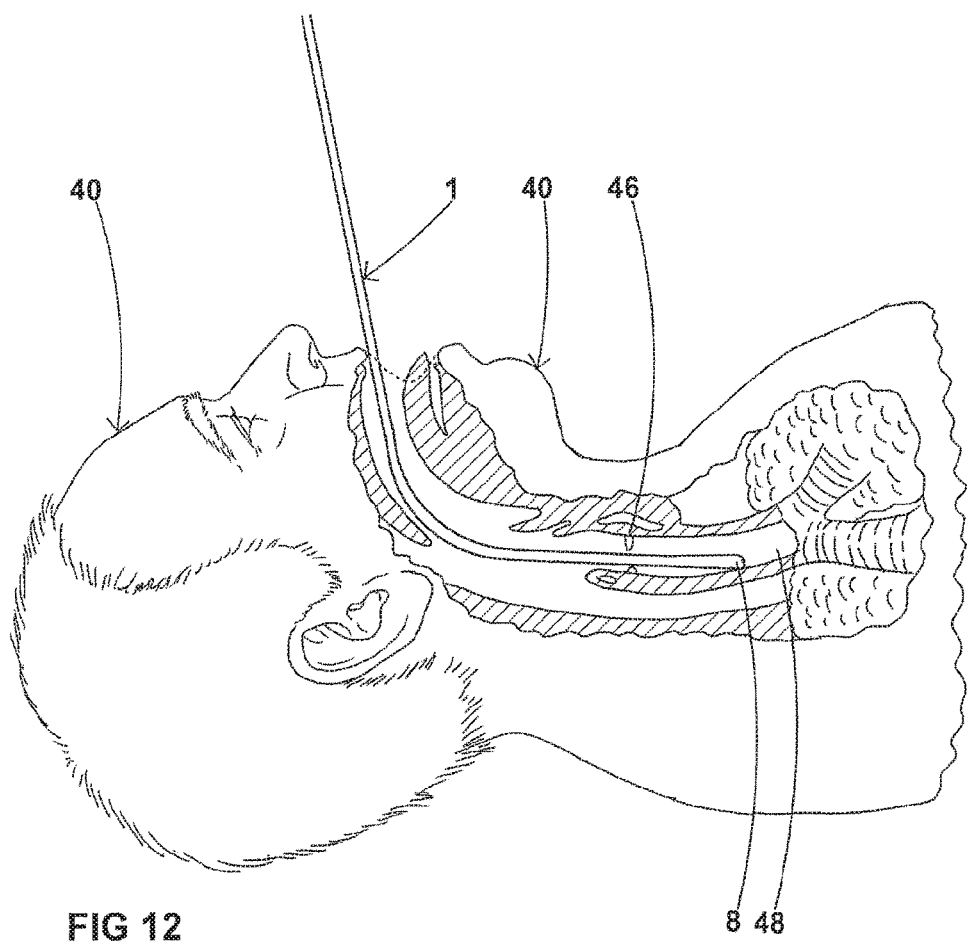
FIG. 12 is a schematic view showing insertion of the tip of the bougie into the trachea of a patient.
Figure 13:
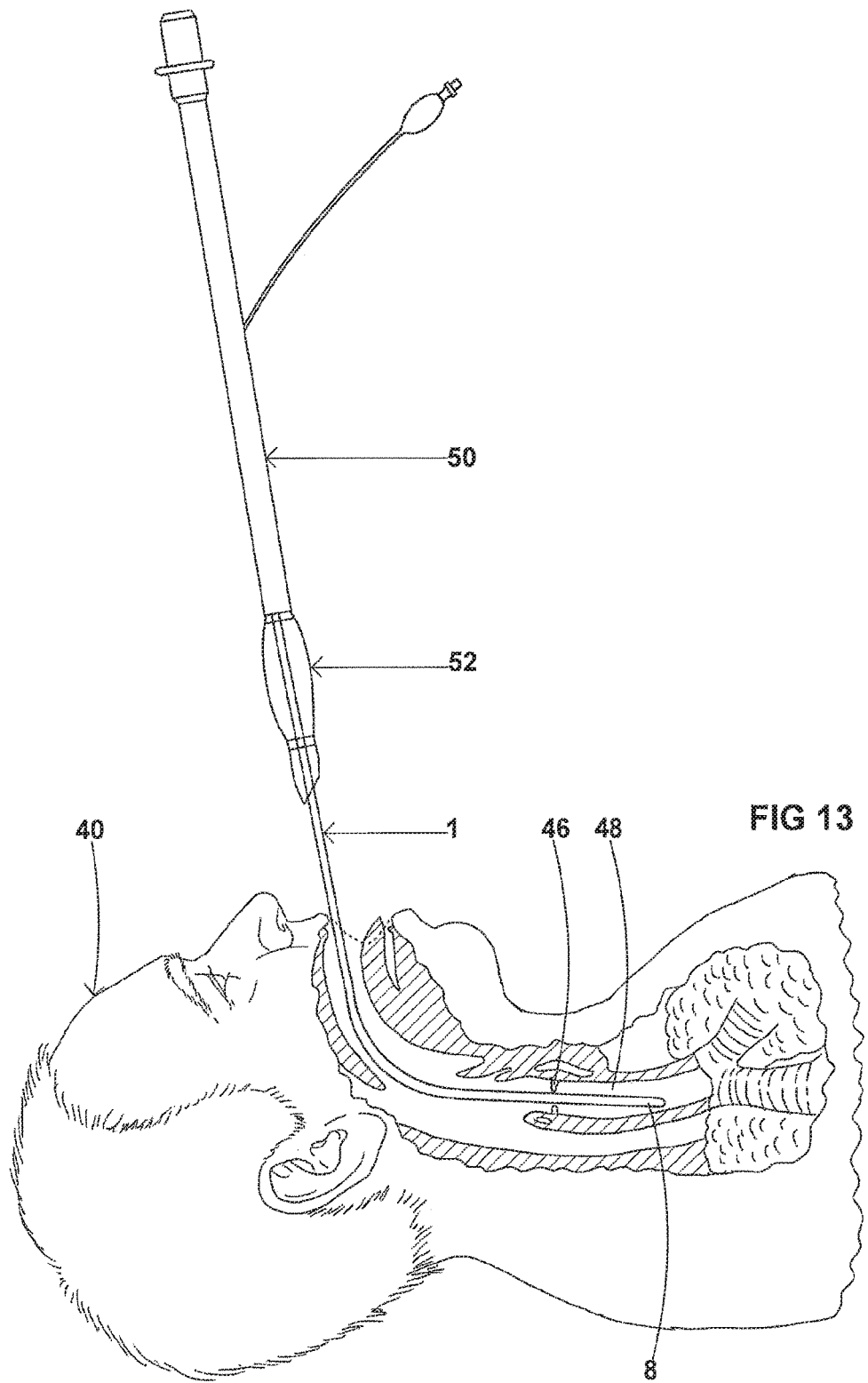
FIG. 13 schematically shows railroading of an ETT on the bougie.

FIGS. 11 to 13 diagrammatically illustrate the manner in which the bougie 1 of the invention can be deployed in a patient 40. In FIG. 11 it will be seen that the hand 42 of an operator can be used to grip the projections 18 so as to enable control of the orientation of the tip 8 relative to the main axis of the shaft 2. In FIG. 11 a laryngoscope 44 is deployed so that the operator has a view of the vocal chords 46 of the patient. During this stage of the deployment, the operator can move the control rod 14 in a proximal or distal direction in order to cause displacement of the tip 8 in an anterior or posterior direction as required in order to best facilitate insertion of the tip through the vocal chords 46. The operator can rotate the main shaft 2 whilst manipulating the control rod so that the tip 8 can be moved through a wide range of positions relative to the anatomy of the patient.

Figure 14:
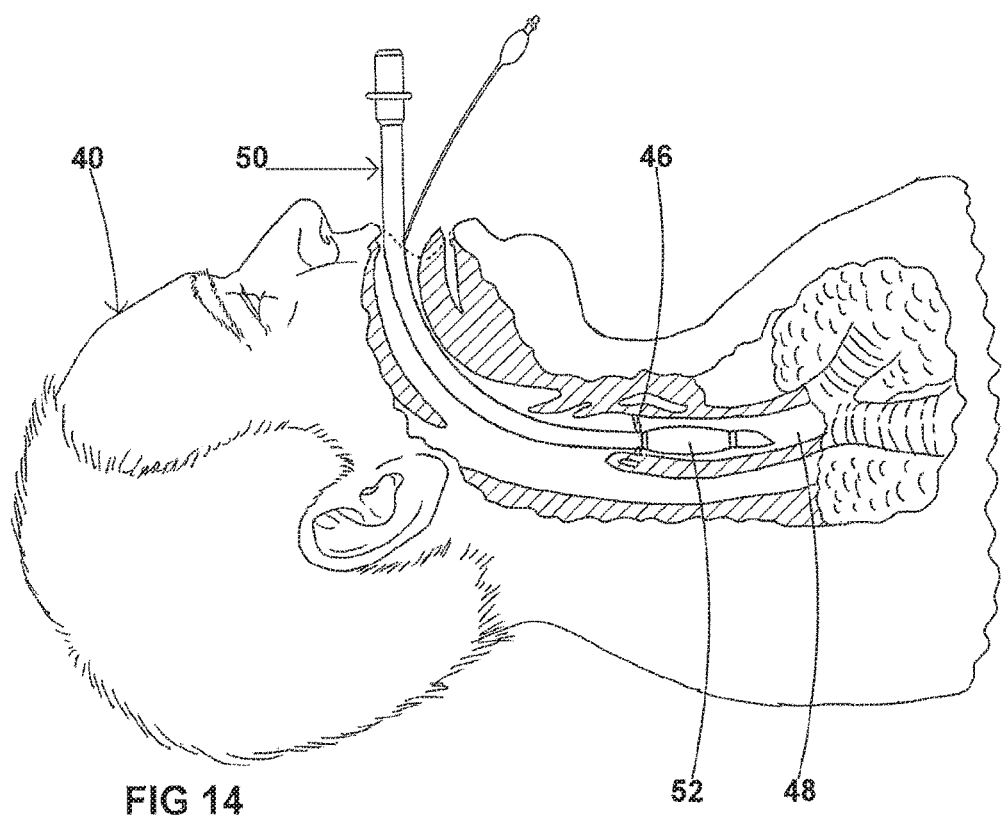
FIG. 14 shows the ETT deployed and the bougie removed from the patient.

In FIG. 12 it will be seen that the tip 8 has passed beyond the chords 46 and into the trachea 48 of the patient. Once in this position, the operator can then mount an endotracheal tube (ETT) 50 over the proximal end of the main shaft 2 of the bougie and then slide the ETT 50 along the length of the main shaft so that its cuff 52 is guided past the vocal chords 46 of the patient and is correctly located in the trachea 48 of the patient. Once in this position, the cuff 52 of the ETT 50 can be inflated and the bougie 1 of the invention removed, as shown in FIG. 14.

FIGS. 15 to 17 illustrate an alternative bougie 51 of the invention which has provision for supplying oxygen to the tip 8. The same reference numerals have been used to denote parts which are the same as or correspond to those of the previous embodiment. It will be seen that the main shaft 2 is in the form of a tube, the interior of which constitutes an oxygen channel 53. The device includes a removable cap 57 which when removed forms an inlet port 62 being the proximal end of the tube which forms the main shaft 2. In this embodiment, the control rod 14 includes a longitudinally extending oxygen channel 55 to permit oxygen to pass from the port 62 along the length of the tube which forms a main shaft 2 and through the body 20 of the tip. The sheath 34 includes an outlet port 58 at its distal end. It will be appreciated that by connecting an oxygen supply tube 54, as shown in FIG. 17, to the port 62 oxygen can be discharged to a patient from the outlet port 58.

FIGS. 18 to 22 diagrammatically illustrate a further bougie 61 constructed in accordance with the invention. The same reference numerals have been used to denote parts which are similar to those of the bougie 51 shown in FIGS. 15 to 17. In this embodiment, the main shaft 2 is in the form of a tubular body 65 which is formed with a longitudinally extending partition 67 which defines two channels 56 and 59. The control rod 14 is slideably mounted in the channel 59 and is generally semi-circular in cross-section so as to neatly fit within the channel 59. The proximal end of the channel 59 includes a barrier 60 which can be formed from a body of silicon adhesive or the like. The channel 59 can be used for introduction of oxygen at the port 62 and the barrier 60 prevents oxygen entering the channel 59. The distal end of the tubular body 65 is formed with an outlet port 58 in the sidewall of the tube which forms the main shaft 2, as shown in FIG. 18. Oxygen can be introduced into inlet port 62 via the oxygen supply tube 54 as before.

It will be appreciated that the bougie 61 of FIGS. 18 to 22 could be used for suction purposes if a source of vacuum were coupled to the port 62. The device could therefore be used for removal of mucous, blood or other fluid from a patient. The port 62 could also be used as a passageway for a guidewire or other instrument to be inserted into the trachea of a patient.

FIGS. 23 to 25 illustrate an alternative bougie 70 constructed in accordance with the invention. The same reference numerals have been used to denote parts which are the same as or correspond to those of previous embodiments. In FIG. 23 the flexible sheath 34 has been omitted for clarity of illustration. The main difference between the bougie 70 and the previous embodiments is that the distal end 30 of the control rod 14 is not directly connected to the tip body 20 but is coupled thereto by means of a wire 68. Preferably, the wire 68 is made from stainless steel and has a diameter of about 0.24 mm. In the illustrated arrangement, the wire 68 may have a length of say 49 mm. It will be appreciated that braided wire could also be used.

The proximal end 72 of the wire 68 is located within a recess 66 formed in the distal end 30 of the control rod. The proximal end of the wire 68 is securely fastened to the control rod by means of a body 69 of adhesive material such as epoxy resin. In the arrangement shown in FIG. 23, the tip body 20 is moulded with a thickened portion 74 on one side thereof where the openings to the slots 22 are located, i.e. opposite to the apices of the slots 22. A bore 76 is formed in the widened portion 74 as best seen in FIG. 25 and the wire 68 can pass through the bore 76 to the distal end 32 of the body 20. In the illustrated arrangement, the distal end 78 of the wire 68 is bent back in the proximal direction so as to extend within the bore 26 of the body 20. A body 71 of adhesive such as epoxy resin is then placed in the bore so as to fix the distal end 78 of the wire to the distal end 32 of the body 20. The bougie 70 operates in a similar manner to the previous embodiments. When the user engages the projections 18 and pulls the control rod in a distal direction, this will be translated into increased tension in the wire 68 which will cause bending of the body 20 laterally owing to the decrease in width of the slots 22. In the illustrated arrangement, when the control rod is moved proximally, the body 20 will be bent downwardly as shown in FIG. 23. On the other hand, if the user pushes the control rod in a distal direction, the wire 68 will be capable of transmitting compressional forces on the end 32 so that it will be bent in the opposite direction, that is to say upwardly as seen in FIG. 23. It will be appreciated that the wire 68 and bore 76 function somewhat analogously to a Bowden cable. A prototype of this arrangement has been made and found to exhibit good flexure of the body 20 with relatively small forces being applied by the user to the projections 18. The ends of the projections 18 can therefore be rounded as shown in FIG. 23 which makes the bougie 70 more convenient to use.

As mentioned above, the main shaft 2 is in the form of a nylon tube. The control rod 14 can also be injection moulded from nylon. The body 20 or sheath 34 is preferably coloured green or yellow so that it can better be seen by a user. Preferably further, the tip body or sheath may include fluorescent pigment (glow in the dark pigment) such as those available through Smooth-On, Inc. of Pennsylvania USA. In some applications, the glow in the dark effect enhances placement of the bougie tip and provides a clear indication that the bougie tip has passed through the vocal chords and into the trachea of a patient. The glow in the dark effect can be enhanced by exposure of the tip to ultraviolet light prior to use.

It will be appreciated that the bougie of the device is simple and inexpensive and can be manufactured as a disposable or single use product.

Many modifications will be apparent to those skilled in the art without departing from the spirit and scope of the invention.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavor to which this specification relates.

LIST OF PARTS

| | |
|---|---|
| bougie | 1 |
| main shaft | 2 |
| proximal end | 4 |
| distal end | 6 |
| displaceable tip | 8 |
| internal bore | 10 |
| longitudinal axis | 12 |
| axis | 13 |
| control rod | 14 |
| recess | 16 |
| lateral projections | 18 |
| tip body | 20 |
| rebate | 21 |
| slots | 22 |
| inner ends | 23 |
| proximal end | 24 |
| bore | 26 |
| portion | 27 |
| plane | 29 |
| distal end | 30 |
| plane | 31 |
| distal end | 32 |
| flexible sheath | 34 |
| distal end | 36 |
| proximal end | 38 |
| patient | 40 |
| hand | 42 |
| laryngoscope | 44 |
| vocal chords | 46 |
| trachea | 48 |
| endotracheal tube | 50 |
| bougie | 51 |
| cuff | 52 |
| oxygen channel | 53 |
| oxygen supply tube | 54 |
| oxygen channel | 55 |
| channel | 56 |
| removable cap | 57 |
| outlet port | 58 |
| channel | 59 |
| barrier | 60 |
| bougie | 61 |
| inlet port | 62 |
| tubular body | 65 |
| recess | 66 |
| partition | 67 |
| wire | 68 |
| body | 69 |
| bougie | 70 |
| body | 71 |
| proximal end | 72 |
| portion | 74 |
| bore | 76 |
| distal end | 78 |

The invention claimed is:

1. A bougie for insertion in a patient, the bougie including:
   (i) a main shaft in the form of a tube having a proximal end and a distal end and a bore extending axially therein;
   (ii) a longitudinally extending recess formed in the main shaft between the proximal and distal ends thereof, and closer to the distal end;
   (iii) a movable tip having a proximal end and a distal end, the proximal end of the movable tip being connected to the distal end of the main shaft;
   (iv) a control member having a proximal end and a distal end, the control member being mounted for sliding movement in the bore of the main shaft;
   (v) lateral projections provided on the control member which are located in the region of said recess;
   the distal end of the control member being coupled to the distal end of the movable tip, the arrangement of the main shaft and lateral projections being such that an operator is able to grip said lateral projections so that the operator is able to slide the control member relative to the main shaft so as to cause displacement of the tip relative to the bore of the main shaft; and
   the arrangement of the main shaft and lateral projections being such that an operator is able to pass the movable tip into the trachea of a patient and then mount the distal end of an endotracheal tube over the proximal end of the main shaft so that the endotracheal tube is able to be correctly located in the trachea of the patient and thereafter the bougie is able to be removed from the endotracheal tube.

2. A bougie as claimed in claim 1, wherein the control member is a control rod.

3. A bougie as claimed in claim 2, wherein the distal end of the control member is coupled to the distal end of the movable tip by means of a control wire.

4. A bougie as claimed in claim 3, wherein the main shaft and movable tip are generally tubular in shape and have a common longitudinal axis when the tip is in a neutral position and wherein the control wire extends in a longitudinal direction but is laterally offset relative to said longitudinal axis.

5. A bougie as claimed in claim 4, wherein the tip includes a passageway through which the control wire passes, wherein the control wire is adapted to transmit tensile and compressive forces to the distal end of the tip.

6. A bougie as claimed in claim 4, wherein the tip includes a tip body with lateral formations which, when the tip body is subject to pulling or pushing by the control rod, causes lateral displacement of the tip in anterior and posterior directions respectively, wherein the tip body is tubular and the lateral formations comprise slots extending laterally through the tubular tip body along one side of the tubular tip body, wherein the control wire is offset towards said one side of the tip body.

7. A bougie as claimed in claim 2, wherein the tip includes a tip body with lateral formations which, when the tip body is subject to pulling or pushing by the control rod, causes lateral displacement of the tip in anterior and posterior directions respectively.

8. A bougie as claimed in claim 7, wherein the tip body is tubular and the lateral formations comprise slots extending laterally through the tubular tip body along one side of the tubular tip body.

9. A bougie as claimed in claim 8, wherein the control rod extends through the tubular tip body and the control rod's distal end is coupled to the distal end of the tubular tip body so that:
   (i) when the operator slides the control rod in a proximal direction relative to the main shaft the tip is displaced in the anterior direction; and
   (ii) when the operator slides the control rod in a distal direction relative to the main shaft the tip is displaced in the posterior direction.

10. A bougie as claimed in claim 7, wherein the tip includes a sheath which covers the tip body.

11. A bougie as claimed in claim 10, wherein the sheath is formed from resilient material and has a closed distal end and a proximal end which is joined to the distal end of the main shaft.

12. A bougie as claimed in claim 7, wherein in a relaxed position of the tip, the tip is axially aligned with the axis of the main shaft, and wherein the tip body is made from resilient material which causes the tip body to return to a position in which the tip body is aligned with the main shaft.

13. A bougie as claimed in claim 2, wherein the bougie further comprises a tip body and a sheath.

14. A bougie as claimed in claim 13, wherein the tip body is integrally formed at the distal end of the main shaft.

15. A bougie as claimed in claim 1, wherein the main shaft and control member are flexible.

16. A bougie as claimed in claim 1, wherein the tip is adapted to be displaced through up to 190° relative to the axial direction of the main shaft.

17. A bougie as claimed in claim 16, wherein the tip is adapted to be displaced through up to 100° in the anterior direction and up to 90° in the posterior direction.

18. A bougie as claimed in claim 1, wherein in a relaxed position of the tip, the tip is axially aligned with the axis of the main shaft.

19. A bougie as claimed in claim 1, including a first port near the proximal end of the main shaft and a second port adjacent to the distal end of the main shaft or in the tip so that, in use, fluids is able to pass into the first port and out of the second port or vice versa.

20. A bougie as claimed in claim 19, wherein the main shaft includes a partition so as to form a first chamber and a second chamber, the control member being movable in the first chamber and wherein the first and second ports are in fluid communication with the second chamber.

21. A bougie as claimed in claim 1, wherein the tip is made from coloured material and/or includes fluorescent pigment.

* * * * *